US00PP19756P3

(12) United States Plant Patent
Ballington et al.

(10) Patent No.: US PP19,756 P3
(45) Date of Patent: Feb. 24, 2009

(54) BLUEBERRY NAMED 'ROBESON'

(50) Latin Name: *Vaccinum*
Varietal Denomination: Robeson

(76) Inventors: James Ralph Ballington, 260 Kilgore Hall, Horticultural Science Department, North Carolina State University, Raleigh, NC (US) 27695-7609; Susan Duke Rooks, Horticultural Crops Research Station, 3800 Castle Hayne Rd., Castle Hayne, NC (US) 28429-6519

( * ) Notice: Subject to any disclaimer, the term of this patent is extended or adjusted under 35 U.S.C. 154(b) by 409 days.

(21) Appl. No.: 11/303,720

(22) Filed: Dec. 19, 2005

(65) Prior Publication Data

US 2007/0143890 P1 Jun. 21, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
*Assistant Examiner*—Georgia Helmer

(57) ABSTRACT

*Vaccinium*×'Robeson' is a new and distinct pentaploid variety of blueberry plant that has the following unique combination of desirable features that are outstanding in a new variety.

1. A ripening season that bridges the gap between highbush and rabbiteye blueberry varieties.
2. Consistent yields of medium size fruit best suited for local direct marketing.
3. Very good fruit quality and good color.
4. Very vigorous plants with upright plant habit and broad soil adaptation, including higher pH soils.

2 Drawing Sheets

Latin name of the genus and species: The Latin name of the novel blueberry plant variety disclosed herein is *Vaccinium*×'Robeson'.

Variety denomination: The inventive hybrid *Vaccinium* plant cultivar disclosed herein is pentaploid with 2n=5X=60 chromosomes and has been given the variety denomination 'Robeson'.

BACKGROUND OF THE INVENTION

The present invention relates to a new and distinct pentaploid hybrid *Vaccinium* (blueberry plant) cultivar grown as a fruiting woody shrub for commercial agriculture. Blueberries are typically consumed both fresh and in a number of processed products.

The new and distinct pentaploid hybrid variety of blueberry (*Vaccinium* Linnaeus) plant originated from the hand pollinated cross of 'US 226' [tetraploid (2n=4x=48 chromosomes), a hybrid of *Vaccinium corymbosum* Linnaeus×*V. myrtilloides* Michaux] (unpatented)× 'Premier'{hexaploid (2n=6X=72 chromosomes) [(*V. virgatum* Aiton (syn. *V. ashei* Reade)]} (unpatented) made in 1980 in Raleigh, N.C. 'US 226' was an early blooming and early ripening genotype that produced medium size and rather soft light blue fruit during highbush blueberry (*V. corymbosum* L.) ripening season on a plant that was highly resistant to phytophthora root rot caused by *Phytophthora cinnamoni*. 'Premier' is the standard early ripening rabbiteye blueberry (*V. virgatum* Ait.) cultivar grown commercially in North Carolina. (Early ripening rabbiteye cultivars start ripening about four weeks after early ripening highbush cultivars.) 'Premier' also blooms early and produces large size high quality light blue fruit that is medium in fruit firmness on a very vigorous plant that is resistant to phytophthora root rot.

Seeds from this hand pollination were germinated in winter 1980/1981 in Raleigh, N.C., and 35 seedlings were established at Jackson Springs, N.C., in 1982. When the seedlings reached maturity in 1986, an elite genotype designated as 'NC 2849' was selected for its vigorous erect plant habit, productivity, fruit size, color, picking scar, firmness, quality and early maturity by James R. Ballington. 'NC 2849' was by far the superior genotype of the two seedlings in the progeny of 35 that produced attractive blue fruit.

During 1987 the original seedling of 'NC 2849' was propagated by hardwood stem cuttings in Raleigh, N.C., and following rooting, single three plant plots were established at Jackson Springs and Fletcher, N.C. in 1988. Based on its performance in these initial trials, in 1996 it was propagated by softwood stem cuttings and established in a replicated trial at Castle Hayne, N.C. It was also established in a grower trial at Ivanhoe, N.C., under a Memorandum of Agreement whereby the grower provided the land and care of the plants and North Carolina State University retained ownership of the variety. Plants and fruit of this new variety have remained true to type through these successive cycles of asexual propagation. This new variety has been named the 'Robeson' cultivar.

SUMMARY OF THE INVENTION

'Robeson' is a new and distinctive pentaploid blueberry plant that differs from its female parent, 'US 226', for leaf and stem pubescence and leaf margins. The stems and abaxial surfaces of the leaves of 'US 226' were densely pubescent and the leaf margin entire. The stems and leaves of 'Robeson' were glabrous and the apical ⅔ of the leaf margins serrulate. 'Robeson' differed from its male parent, 'Premier', for internode length of first flush growth, number of renewal stems, dormant stem color on the unexposed stem surface, first flush stem color in summer, presence of leaf glands, fruit shape and number of seeds per berry. 'Premier' had a first flush internode length of 18 cm compared to 11 cm for 'Robeson'. 'Premier' had three renewal stems per plant and 'Robeson' one. The dormant stem color on the unexposed surface was green for 'Premier' and yellow-green for 'Robeson'. The first flush summer stem color of 'Premier' was yellow-green and green for 'Robeson'. The abaxial leaf surface of leaves of 'Premier' have sparse stalked glands along lateral veins while the leaves of 'Robeson' were eglandular. 'Robeson' had only about ⅓ the number of seeds per berry as 'Premier'.

'Robeson' begins ripening somewhat earlier than its 'Premier' parent, and bridges the gap between late ripening highbush blueberry cultivars and early ripening rabbiteye blueberry cultivars. The plant is very vigorous and upright with very broad soil adaptation, including higher pH soils. Yield is good and similar to Premier. Fruit size was medium and similar to 'Tifblue'. Firmness was only average and similar to 'Premier', so that it was not adaptable to mechanical harvesting for the fresh market. Fruit color was equal to 'Premier' based on the R.H.S. color chart, but not quite as good based on Minolta Color Meter determinations. Fruit quality ratings for 'Robeson' showed it to be superior to 'Premier' and equal to 'Tifblue', but not quite equal to 'Columbus'. Short shelf-life of fruit indicated that it was best suited for local direct marketing outlets. Leaves were narrowly elliptic-obovate in shape and both the leaf base and apex angles acute. The flowers were not self-fertile and produced very little viable pollen. The corolla of individual flowers was white and cylindro-urceolate in shape. The fruit was round-oblate in shape and the calyx not prominent and appressed to the apex of the fruit. 'Robeson' is readily asexually propagated by either softwood or hardwood stem cuttings and has remained true to type through successive generations of asexual propagation. The chilling requirement of dormant buds on 'Robeson' plants is 400 to 600 hours below 45° F. It is susceptible to stem canker, but has not had any problems to date with stem blight. It is resistant to phytophthora root rot.

BRIEF DESCRIPTION OF THE DRAWINGS

The photographs in the drawings were made using digital photography techniques, and illustrates the colors as true as reasonably possible when using these techniques. Colors in the photographs may differ slightly from the color values cited in the detailed botanical description, which accurately describe the colors of the new pentaploid hybrid *Vaccinium* plant variety. All photographs were taken from nine year old plants growing at Castle Hayne, N.C.

FIG. 1 shows the typical plant habit of 'Robeson'.

FIG. 2 shows the typical fruit of 'Robeson'.

DETAILED BOTANICAL DESCRIPTION OF THE VARIETY

The following is a detailed botanical description of a new and distinct pentaploid hybrid variety of *Vaccinium* Linnaeus plant known as 'Robeson'. The observations below are from mature plants grown in test plots at a standard commercial spacing of 4' between plants in rows and 10' between rows, at Castle Hayne, N.C. Those skilled in the art of cultivar description and evaluation will appreciate that certain characteristics of a variety will vary with older or, conversely, with younger plants. 'Robeson' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length and cultural conditions. Color notations are based on The Royal Horticultural Society Colour Chart, The Royal Horticultural Society, London, UK, 1995 edition.

For botanical description purposes, 'Robeson' was compared to its 'Premier' parent. The botanical descriptive data presented are averages of data collected from mature nine year old plants growing in a replicated trial at Castle Hayne, N.C., in 2005. The exception to using average values was with seed numbers where these were determined from a representative fruit of each cultivar.

Plant:

*Dimensions.*—'Robeson' — 1.6 m height, 1.4 m diameter, H/D ratio 1.14. 'Premier' — 1.9 m height, 1.5 m diameter, H/D ratio 1.27.

*Growth habit.*—Upright for 'Robeson' (FIG. 1) and 'Premier'.

*Vigor.*—Very good for 'Robeson' and 'Premier'.

*Plant adaptation.*—'Robeson' and 'Premier' are both very broadly adapted to soils including higher pH soils.

*Mature cane diameter.*— 4.4 cm for 'Robeson' and 'Premier'.

*Mature cane length.*—'Robeson' — 1.1 m. 'Premier' — 1.5 m.

*Internode length on first flush growth.*—'Robeson' — 11.0 cm. 'Premier' — 18.0 cm.

*Number of renewal stems.*—'Robeson' — 1.0. 'Premier' — 3.0.

*Dormant mature stem color.*—Grayed-green (RHS 198D) for 'Robeson' and 'Premier'.

*Dormant one year stem color.*—'Robeson' — red (RHS 53B) on the exposed surface, yellow-green (RHS 148B) on the unexposed surface. 'Premier' — red (RHS 53B) on the exposed surface, green (RHS 137D) on the unexposed surface.

*First flush growth stem color in summer.*—'Robeson' — green (RHS 138C). 'Premier' — yellow-green (RHS 147C).

*Pubescence on summer and one year dormant stems.*—No stem pubescence on 'Robeson' or 'Premier'.

Leaves:

*Leaf blade dimensions.*—'Robeson' — length 81 mm, width 41 mm, L/W ratio 1.98. 'Premier' — length 81 mm, width 34 mm, L/W ratio 2.38.

*Leaf petiole length.*—'Robeson' — 4 mm. 'Premier' — 3 mm.

*Leaf shape.*—'Robeson' — narrowly elliptic-obovate. 'Premier' — narrowly elliptic-obovate to oblanceolate.

*Leaf apex angle.*—'Robeson' — acuminate to acute. 'Premier' — acuminate.

*Leaf base angle.*—Acute for 'Robeson' and 'Premier'.

*Leaf margin.*—'Robeson' — apical ⅔ serrulate. 'Premier' — serrulate.

*Leaf pubescence.*—None for Robeson and Premier.

*Leaf glands.*—'Robeson' — none. 'Premier' — sparse stalked glands along lateral veins on the abaxial surface.

*Leaf color.*—The adaxial surface color is green (RHS 137A) and the abaxial color green (RHS 138B) for 'Robeson' and 'Premier'.

Flowers:

*Number of petals.*—Five, fused into a corolla tube for 'Robeson' and 'Premier'.

*Number of flowers per inflorescence.*—'Robeson' — 4.0. 'Premier' — 4.0.

*Flower dimensions.*—'Robeson' — length 9.0 mm, diameter 5.0 mm, L/D ratio 1.8. 'Premier' — length 9.0 mm, diameter 4.0 mm, L/D ratio 2.2.

*Length of the single style.*—'Robeson' and 'Premier' — 8.0 mm.

*Flower shape.*—'Robeson' — cylindro-urceolate. 'Premier' — cylindraceous to cylindro-urceolate.

*Flower color.*—'Robeson' — red-purple (RHS 63B) on the basal half and mainly on the petal lobes just prior to opening, fading to white (RHS 155C) when fully open. 'Premier' — red-purple (RHS 63D) just prior to opening, fading to white (RHS 155C) on fully open flowers.

Fruit:

*Fruit dimensions.*—'Robeson' — length 15 mm, diameter 17 mm, L/D ratio 0.88. 'Premier' — length 15 mm, diameter 18 mm, L/D ratio 0.83.

*Fruit shape.*—'Robeson' — round-oblate. 'Premier' — oblate.

*Fruit pedicel length.*—'Robeson' and 'Premier' — 8 mm.

*Fruit picking scar.*—'Robeson' — 2.0 mm diameter, dry. 'Premier' — 1.0 mm diameter, dry.

*Fruit calyx orientation and prominence.*—Appressed against the apical end of the fruit and not prominent for 'Robeson' And 'Premier'.

*Fruit color with bloom* (*epicuticular wax*).—'Robeson' (FIG. 2) and 'Premier' — violet-blue (RHS 97B).

*Fruit color without bloom.*—Black (RHS 202A) for 'Robeson' and 'Premier'.

Seeds:

*Number of fully developed seeds per berry.*—'Robeson' — 14. 'Premier' — 46.

*Seed dimensions.*—'Robeson' — length 1.50 mm, width 1.00 mm, L/W ratio 1.5. 'Premier' — length 2.00 mm, width 1.00 mm, L/W ratio 2.0.

*Seed shape.*—Basically depressed-ovate for 'Robeson' and 'Premier'.

For technical (pomological) descriptive data purposes 'Robeson' was compared to 'Premier', 'Columbus' (unpatented) and 'Tifblue' (unpatented) at Castle Hayne, N.C., in Tables 2–7. The exception was for time of flowering, where the data was more representative from Jackson Springs, N.C., in 1992, and compared 'Robeson' with 'Premier' and 'Tifblue' (Table 1).

Time of flowering: 'Robeson' was a few days later than 'Premier' for date of first bloom and a few days later for date of 50% bloom (Table 1). It was just over a week earlier than 'Tifblue' for both first bloom and 50% bloom.

TABLE 1

Time of flowering of blueberry cultivars at Jackson Springs, NC. 1992.

| Cultivar | Date of first bloom | Date of 50% bloom |
|---|---|---|
| Robeson | 3/23 | 4/11 |
| Premier | 3/21 | 4/14 |
| Tifblue | 4/1 | 4/20 |

Pollination requirements: The flowers of 'Robeson' are not self-fertile and require cross-pollination to set commercial crops of fruit. 'Premier' has a bloom pattern similar to 'Robeson' and has proved to be an excellent pollinator for this variety.

Pollen production: 'Robeson' flowers produce very little viable pollen since the variety is pentaploid.

Season of ripening: 'Robeson' was somewhat earlier ripening than 'Premier' and much earlier ripening than either 'Columbus' and 'Tifblue' (Table 2).

TABLE 2

Season of ripening for blueberry cultivars at Castle Hayne, NC.

| | Cumulative percent ripe by June 29th[1] | | | |
|---|---|---|---|---|
| Cultivar | 1999 | 2000 | 2001 | Average |
| Robeson | 100 | 100 | 100 | 100 |
| Premier | 86 | 100 | 93 | 93 |
| Columbus | 40 | 57 | 33 | 43 |
| Tifblue | 42 | 0 | 0 | 14 |

[1]Percent ripe after the first two weeks of the season.

Yield per plant: In 1999 and 2001 there were no significant differences between 'Robeson' and the other three varieties for yield, and yield was quite good for all four in 2001 (Table 3). Yield in 2000 was adversely affected by the harvest method (rubber hoses) due to excessive fruit falling to the ground, so the significant differences indicated were not meaningful.

TABLE 3

Yield of blueberry cultivars at Castle Hayne, NC.

| | Yield (lbs./plant)[1] | | |
|---|---|---|---|
| Cultivar | 1999 | 2000[2] | 2001 |
| Robeson | 4.6 | 3.1bc | 15.2 |
| Premier | 6.6 | 4.8b | 15.8 |
| Columbus | 5.5 | 11.2a | 19.8 |
| Tifblue | 6.8 | 9.0a | 18.3 |

[1]Values not followed by the same letter(s) are significantly different at the 0.05 level (Duncan's Multiple Range Test).
[2]Yield adversely affected by harvest method (catch frames and rubber hoses).

Fruit size (weight per berry): Fruit size of 'Robeson' was equal to 'Tifblue' two years out of three, and 'Premier' one year out of three (Table 4). It had the smallest average size of the four varieties. 'Robeson' therefore has medium size fruit suitable for mechanical harvesting.

TABLE 4

Fruit size of blueberry cultivars at Castle Hayne, NC.

| Cultivar | Fruit size (weight per berry in grams)[1] 1999 | 2000 | 2001 | Average |
|---|---|---|---|---|
| Robeson | 1.13c | 1.46bc | 1.35c | 1.31 |
| Premier | 1.72b | 1.56b | 1.78b | 1.69 |
| Columbus | 2.07a | 2.08a | 2.12a | 2.09 |
| Tifblue | 1.64b | 1.41c | 1.36c | 1.47 |

[1]Values not followed by the same letter(s) are significantly different at the 0.05 level (Duncan's Multiple Range Test).

Fruit color: In addition to The Royal Horticultural Society Colour Chart, fruit color was also determined objectively with a Minolta Color Meter (Table 5), and these data indicated that 'Robeson' was equal to 'Tifblue' for color, but not to equal to 'Premier' or 'Columbus' by this means of comparison.

TABLE 5

Fruit color and fruit firmness of blueberry cultivars at Castle Hayne, NC.

| Cultivar | Color[1,2] 2001 | Firmness[1,3] 1999 | 2001 |
|---|---|---|---|
| Robeson | 17.8c | 98b | 115c |
| Premier | 20.7b | 104ab | 133b |
| Columbus | 23.4a | 102ab | 137b |
| Tifblue | 19.9bc | 115a | 175a |

[1]Values not followed by the same letter(s) are significantly different at the 0.05 level (Duncan's Multiple Range Test).
[2]Color (lightness or "L" values) determined objectively by a Minolta Color Meter. Higher values indicate lighter blue color.
[3]Fruit firmness determined objectively using a Firm-tech Firmness Tester.

Fruit firmness: Fruit firmness determined by a Firm-tech Firmness Tester demonstrated that 'Robeson' was equal to 'Premier' and 'Columbus' in 1999 (Table 5), but it was significantly less firm than the other three varieties in 2001. Therefore, even though fruit size of 'Robeson' is in the appropriate range for mechanical harvest, the fruit is not sufficiently firm to mechanically harvest for the fresh market, and would only be appropriate for processing markets following mechanical harvesting.

Fruit flavor: Subjective ratings for flavor indicated that 'Robeson' consistently scored in the very good range (Table 6), and fruit quality is definitely one of this variety's strong points. It was significantly better than 'Premier' in all three years, and equal to or better than 'Tifblue' all three years. It was only equal to 'Columbus' one year out of three.

TABLE 6

Fruit flavor of blueberry cultivars at Castle Hayne, NC.

| Cultivar | Flavor[1,2] 1999 | 2000 | 2001 |
|---|---|---|---|
| Robeson | 79a | 77bc | 78b |
| Premier | 75c | 75d | 77c |
| Columbus | 79a | 79a | 80a |
| Tifblue | 77b | 77bc | 78b |

[1]Values not followed by the same letter(s) are significantly different at the 0.05 level (Duncan's Multiple Range Test).
[2]Subjective ratings based on a 0-90 scale, where less than 60 is unsatisfactory, 60-69 is satisfactory, 70-79 is average to good, and 80 and above superior.

Post harvest shelf-life: Post harvest shelf-life of fruit is not one of the strongest characteristics of 'Robeson' (Table 7). It was significantly poorer than the other three varieties following seven days storage at both temperatures. Therefore it is most strongly recommended for production for local direct markets.

TABLE 7

Post harvest shelf-life of the fruit of blueberry cultivars at Castle Hayne, NC. in 2001.

| Cultivar | Percent marketable fruit after seven days[1] 50° F. | 70° F. |
|---|---|---|
| Robeson | 46c | 10c |
| Premier | 70b | 25b |
| Columbus | 84a | 69a |
| Tifblue | 81a | 77a |

[1]Values not followed by the same letter(s) are significantly different at the 0.05 level (Duncan's Multiple Range Test).

Propagation: 'Robeson' is easily propagated asexually by both hardwood and softwood stem cuttings.

Chilling requirement: The chilling requirement of dormant leaf and flower buds on 'Robeson' plants is 400 to 600 hours below 45° F.

Disease reaction: 'Robeson' has not had any problems with stem blight (*Botryospaeria dothidea*) one of the two major diseases affecting blueberries in North Carolina. It is susceptible to the other major disease, stem canker (*Botryosphaeria corticis*). It is also resistant to phytophthora root rot (*Phytophthora cinnamoni*).

That which is claimed is:

1. A new and distinct variety of commercial blueberry plant (*Vaccinium*×'Robeson') substantially as illustrated and described, characterized by its broad soil adaptation, early ripening, high yields, very good fruit quality, medium fruit size, limited numbers of seeds per fruit, and adaptation to direct market outlets.

* * * * *

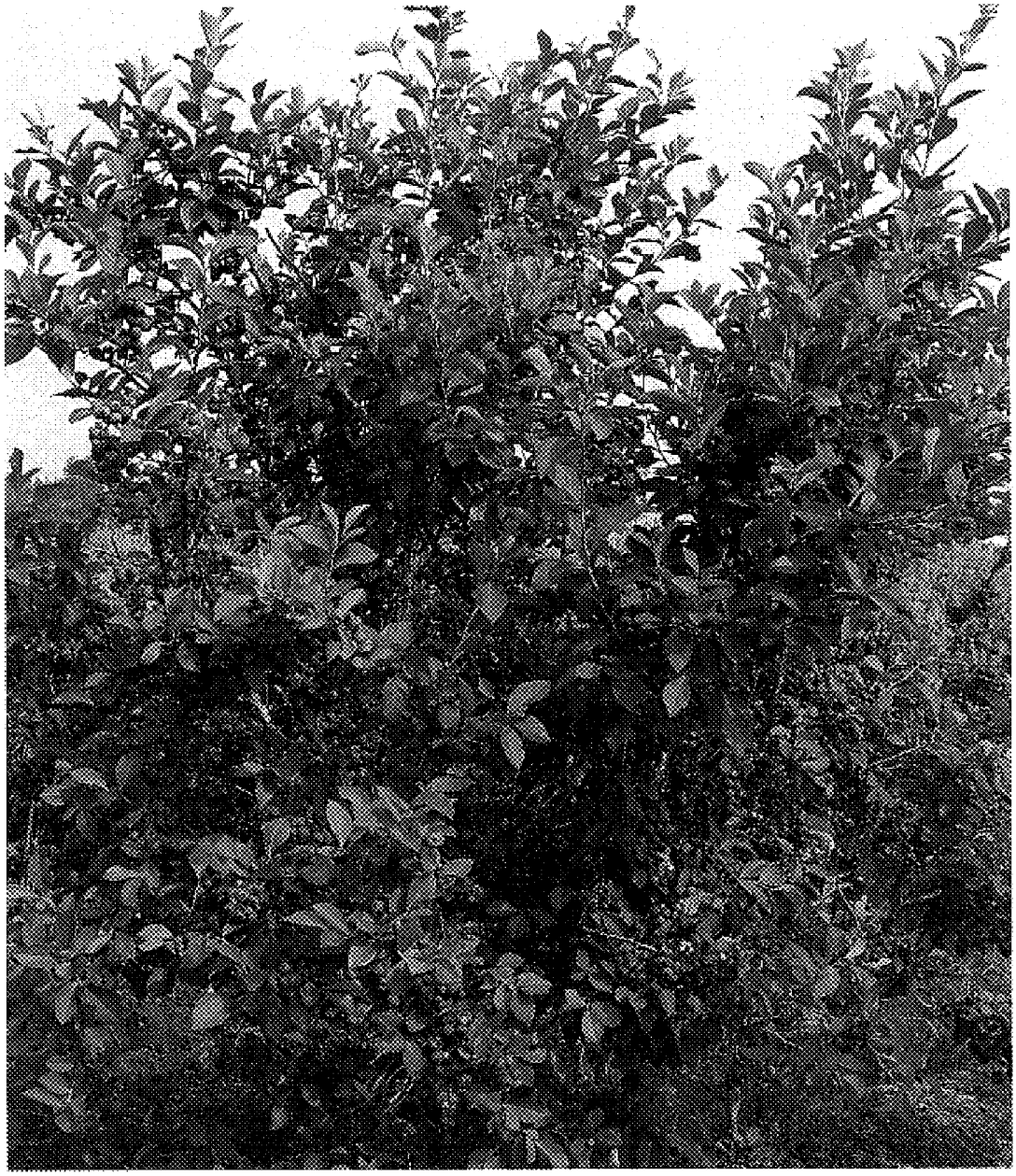

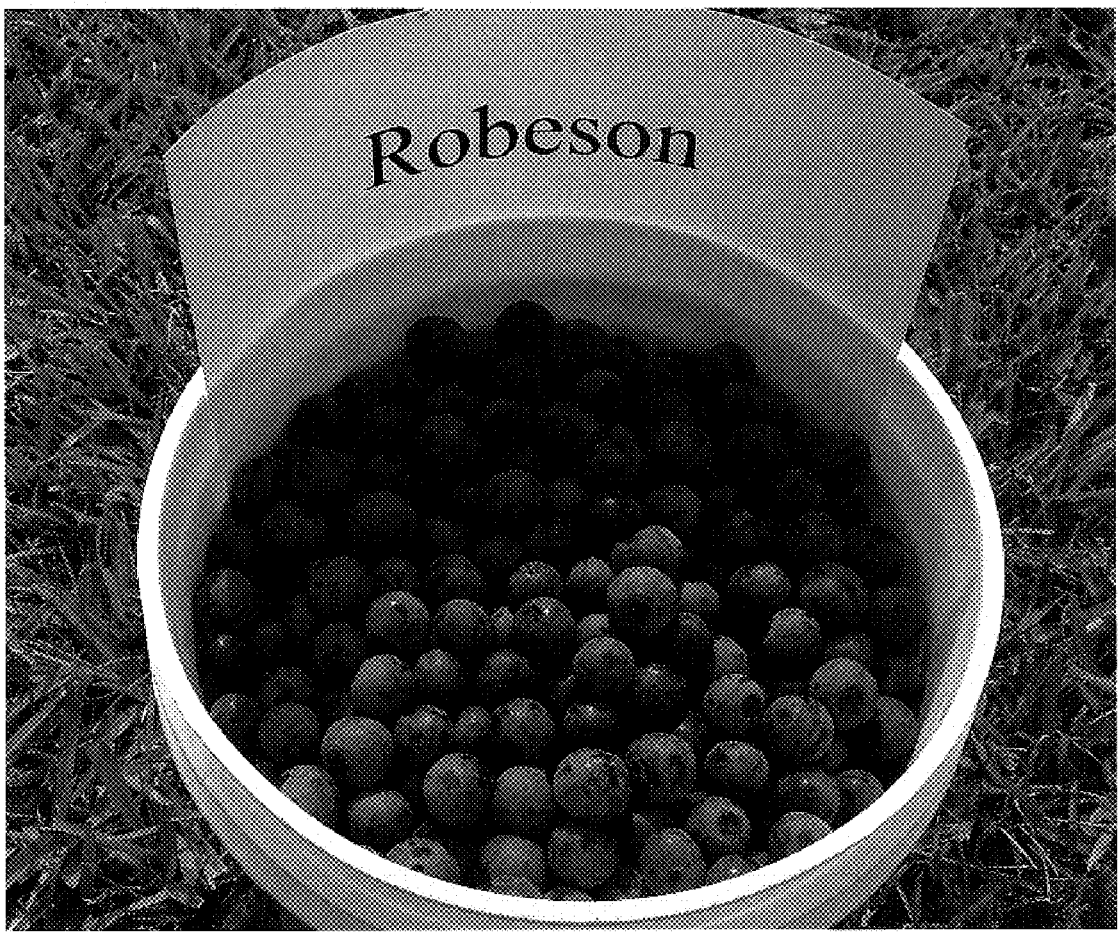
Robeson